United States Patent
Weber

(10) Patent No.: US 7,399,394 B2
(45) Date of Patent: Jul. 15, 2008

(54) ELECTROPHORESIS DEVICE, ELECTROPHORESIS METHOD USING AN ELECTROPHORESIS DEVICE AND USE OF THE ELECTROPHORESIS DEVICE

(75) Inventor: Gerhard Weber, Kirchheim (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 571 days.

(21) Appl. No.: 10/450,830

(22) PCT Filed: Dec. 7, 2001

(86) PCT No.: PCT/EP01/14389

§ 371 (c)(1),
(2), (4) Date: Jun. 18, 2003

(87) PCT Pub. No.: WO02/51115

PCT Pub. Date: Jun. 27, 2002

(65) Prior Publication Data

US 2004/0026251 A1 Feb. 12, 2004

(30) Foreign Application Priority Data

Dec. 18, 2000 (DE) .............................. 100 63 096

(51) Int. Cl.
*G01N 27/447* (2006.01)
*G01N 27/453* (2006.01)
(52) U.S. Cl. ................. 204/450; 204/456; 204/465; 204/600; 204/606; 204/615
(58) Field of Classification Search ................. 204/450, 204/456, 465, 600, 606, 616, 615
See application file for complete search history.

(56) References Cited

U.S. PATENT DOCUMENTS

| 2,555,487 A | 6/1951 | Haugaard et al. |
| 2,878,178 A | 3/1959 | Bier |
| 3,085,956 A | 4/1963 | Caplan |
| 3,125,500 A | 3/1964 | Grassman et al. |
| 3,140,714 A | 7/1964 | Murphy, Jr. et al. |
| 3,149,060 A | 9/1964 | Dobry et al. |

(Continued)

FOREIGN PATENT DOCUMENTS

EP 0081375 B1 4/1989

(Continued)

OTHER PUBLICATIONS

JPO abstract of Muroi et al. (JP 61162741 A).*

(Continued)

*Primary Examiner*—Alex Noguerola
(74) *Attorney, Agent, or Firm*—Mark Lindsey

(57) ABSTRACT

An electrophoresis device having a separation chamber that is provided with at least one sample inlet on the inlet side and outlets (9) for the electrophoretically treated sample species on the outlet side. The separation chamber is divided into two chamber parts (7, 8) by at least one separation element (2) which is selectively permeable for specific sample species and has a continuous inner space extending longitudinally, especially a hollow fiber, from the inlet to the outlet side. Electrodes (4) are disposed parallel to the separation element on both sides of the separation chamber.

13 Claims, 6 Drawing Sheets

U.S. PATENT DOCUMENTS

| | | | |
|---|---|---|---|
| 3,287,244 A | 11/1966 | Mel | |
| 3,320,148 A | 5/1967 | Skeggs | |
| 3,320,149 A | 5/1967 | Isreeli | |
| 3,412,007 A | 11/1968 | Strickler | |
| 3,412,008 A | 11/1968 | Strickler | |
| 3,458,427 A | 7/1969 | Strickler | |
| 3,458,428 A | 7/1969 | Huebner | |
| 3,498,905 A | 3/1970 | Strickler | |
| 3,509,035 A | 4/1970 | Huebner | |
| 3,519,549 A | 7/1970 | Grassmann et al. | |
| 3,616,455 A | 10/1971 | von Munchausen | |
| 3,655,541 A | 4/1972 | Strickler | |
| 3,663,395 A | 5/1972 | Strickler | |
| 3,668,107 A | 6/1972 | Lappe | |
| 3,755,132 A | 8/1973 | Kolin et al. | |
| 3,758,395 A | 9/1973 | Strickler | |
| 3,821,102 A | 6/1974 | Fletcher et al. | |
| 3,847,773 A | 11/1974 | Snyder | |
| 3,989,613 A | 11/1976 | Gritzner | |
| 4,043,895 A | 8/1977 | Gritzner | |
| 4,061,560 A | 12/1977 | Hannig et al. | |
| 4,107,027 A | 8/1978 | Muckenmuller et al. | |
| 4,141,809 A | 2/1979 | Aitchison et al. | |
| 4,204,929 A | 5/1980 | Bier | |
| 4,214,981 A | 7/1980 | Giddings | |
| 4,310,408 A | 1/1982 | Rose et al. | |
| 4,358,358 A | 11/1982 | Rhodes | |
| 4,362,612 A | 12/1982 | Bier | |
| 4,383,905 A | 5/1983 | Richman | |
| 4,394,246 A | 7/1983 | Richman et al. | |
| 4,440,638 A | 4/1984 | Judy et al. | |
| 4,465,582 A | 8/1984 | Richman | |
| 4,749,458 A | 6/1988 | Muroi et al. | |
| 4,874,507 A | 10/1989 | Whitlock | |
| 4,897,169 A | 1/1990 | Bier et al. | |
| 5,032,247 A | 7/1991 | Tarnopolsky | |
| 5,071,536 A | 12/1991 | Ivory | |
| 5,087,338 A | 2/1992 | Perry et al. | |
| 5,114,555 A * | 5/1992 | Stimpson | 204/601 |
| 5,131,994 A | 7/1992 | Shmidt et al. | |
| 5,133,844 A | 7/1992 | Stevens | |
| 5,180,480 A | 1/1993 | Manz | |
| 5,277,774 A | 1/1994 | Shmidt et al. | |
| 5,336,387 A | 8/1994 | Egen et al. | |
| 5,439,571 A | 8/1995 | Sammons et al. | |
| 5,447,612 A | 9/1995 | Bier et al. | |
| 5,482,613 A * | 1/1996 | Boquet | 264/259 |
| 5,540,826 A | 7/1996 | Bier et al. | |
| 5,562,812 A | 10/1996 | Carlson et al. | |
| 5,906,724 A | 5/1999 | Sammons et al. | |
| 5,972,190 A | 10/1999 | Richman | |
| 6,210,574 B1 | 4/2001 | Sammons et al. | |
| 6,328,868 B1 | 12/2001 | Weber | |
| 6,749,733 B1 | 6/2004 | Sibbett | |
| 6,758,953 B2 | 7/2004 | Thomas et al. | |
| 6,793,791 B2 | 9/2004 | Bier | |
| 2001/0040095 A1 | 11/2001 | Shimizu et al. | |
| 2001/0040096 A1 | 11/2001 | Yamamoto et al. | |
| 2002/0008027 A1 | 1/2002 | Rhodes et al. | |
| 2004/0031683 A1 | 2/2004 | Eipel et al. | |
| 2004/0045826 A1 | 3/2004 | Weber | |
| 2004/0050697 A1 | 3/2004 | Eckerson et al. | |
| 2004/0050698 A1 | 3/2004 | Eckerson et al. | |
| 2004/0101973 A1 | 5/2004 | Weber | |
| 2004/0163956 A1 | 8/2004 | Bier | |

FOREIGN PATENT DOCUMENTS

| | | |
|---|---|---|
| EP | 0323 948 A | 7/1989 |
| EP | 0 491 528 A | 6/1992 |
| JP | 061095241 A | 5/1986 |
| JP | 061162741 A | 7/1986 |
| JP | 61162741 A * | 7/1986 |
| JP | 061215952 A | 9/1986 |
| JP | 061215953 A | 9/1986 |
| JP | 063067557 A | 3/1988 |
| JP | 063117252 A | 5/1988 |
| JP | 06130035 A | 5/1994 |
| JP | 2001091497 A | 6/2001 |
| JP | 2001153841 A | 6/2001 |
| JP | 2003247980 A | 9/2003 |
| JP | 2004113079 A | 4/2004 |
| WO | WO 91/04085 A | 4/1991 |
| WO | 9110129 | 7/1991 |
| WO | 04077039 | 9/2004 |

OTHER PUBLICATIONS

Cordero B M et al: "Analytical Applications of Membrane Extraction in Chromatography and Electrophoresis" Journal of Chromatography, Elsevier Science Publishers B.V. Amsterdam, NL. vol. 902, No. 1 Nov. 24, 2000.

* cited by examiner

Fig. 9A
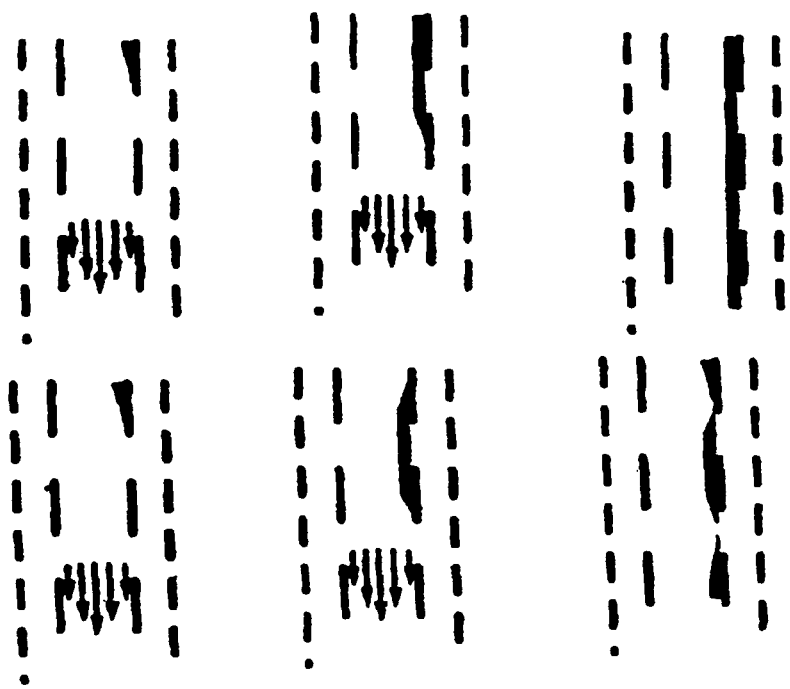
Fig. 9B
Fig. 9C

ELECTROPHORESIS DEVICE, ELECTROPHORESIS METHOD USING AN ELECTROPHORESIS DEVICE AND USE OF THE ELECTROPHORESIS DEVICE

This application is a 371 of PCT/EP01/14389, filed Dec. 7, 2001, which claims priority on German (DE) Patent Application No. 100 63 096.0 filed Dec. 18, 2000, the disclosure of which is hereby incorporated by reference.

BACKGROUND OF THE INVENTION

1. Field of the Invention

The invention relates to an electrophoresis device, an electrophoresis method using an electrophoresis device and the use of the electrophoresis device.

2. Description of Related Art

Electrophoresis devices and electrophoretic separation methods are known in which sample substances are fractionated, at the interface between the liquid phase and the solid phase, into the individual sample species.

An analogous separation method, namely pressure filtration, has already been used in industry on a broad scale and is widely used to separate biopolymers. In comparison, electrophoretic separation, i.e., the so-called electrophoretic filtration process or, in short, electrofiltration is used rarely on the whole, although this process appears to be particularly advantageous. In contrast to pressure filtration, it is not the entire sample volume but only the ionic species and not the entire volume of the solvent which need to be transported during the electrophoretic transfer via the separation membrane provided in the separation chambers of the corresponding electrophoresis device. The reason for the rare application of the electrofiltration process is based on the fact that problems occur in particular during the separation of biopolymers according to this process. These problems appear to reside, inter alia, in the irreversible sorption and denaturisation of the biopolymers. The restriction imposed on electrofiltration by technical problems in the optimum dissipation of the heat, which arises during the electrophoretic process and in the changes in the separation characteristics of the material of the solid phase, i.e., the separation membrane.

Irreversible sorption at the interface between the liquid phase and the solid phase, i.e., the separation membrane, can be largely minimized by using biocompatible synthetic resin membranes. However, it has so far not been possible to prevent the change in the separating characteristics of the membrane after a prolonged period of contact with the biopolymers to be separated, which is referred to as "fouling."

The problems which occur during the use of electrofiltration as a result of the heat development inherent in this separation process decisively restrict, in practice, both the application range of this process and the quantitative throughput in comparison with pressure filtration. In the case of an unfavourable increased development of heat in the material of the separation membrane, the characteristic separation properties can be significantly altered and, as a result, the material can even be destroyed as a result of overheating.

Moreover, electrophoretic separation methods for separating bioparticles in aqueous solution, which are referred to as carrierless electrophoresis or free flow electrophoresis (FFE), and corresponding electrophoretic separation devices are known. During this electrophoretic separation of bioparticles in aqueous solution, media with a high conductivity need to be used in order to maintain the vitality of the bioparticles during and after separation. For this purpose, it is necessary inter alia to solve the problem of the optimum removal of heat from the separation chamber since rising temperatures in the separation chamber cause a substantial deterioration in the separation performance. This means that, for an optimization to be achieved, the temperature gradients at every point in the separation chamber gap as well as the temperature differences at the different points in the separation space need to be minimized. In order to improve the separation performance of FFE, the separation of the bioparticles must also take place with the electrical field strengths being as high as possible which, as a result of the high conductivity of the media, leads to a more than proportional increase in the process heat evolved during the separation process.

The electrophoresis devices available on the market for separating bioparticles, which operate according to the FFE process, have therefore been optimized insofar as, on the one hand, an electrical field strength necessary for the desired separation performance was used and, simultaneously, an optimum elimination of the process heat was achieved by selecting as small a separation chamber gap as possible. In European Patent EP 0 443 024 B1, an electrophoresis device with longitudinal hollow fibres is used to pass through a cooling medium.

SUMMARY OF THE INVENTION

The present invention is directed to creating a high performance electrophoresis device operating at high speed.

The electrophoresis device according to the invention operates according to a combined process of electrofiltration and FFE such that the electrofiltration is carried out under the boundary conditions of an optimized FFE separation process permitting a rapid electrofiltration process and simultaneously avoiding the problems, caused by overheating, of the change in the separation characteristics and a possible destruction of the membrane material.

In the following, particularly preferred practical examples of the invention are described in further detail with reference to the accompanying drawings.

BRIEF DESCRIPTION OF THE DRAWINGS

FIGS. 9A to 9C are diagrammatic representations of the method of operation of the electrophoresis device according to the invention.

DETAILED DESCRIPTION OF THE INVENTION

Figure 1:
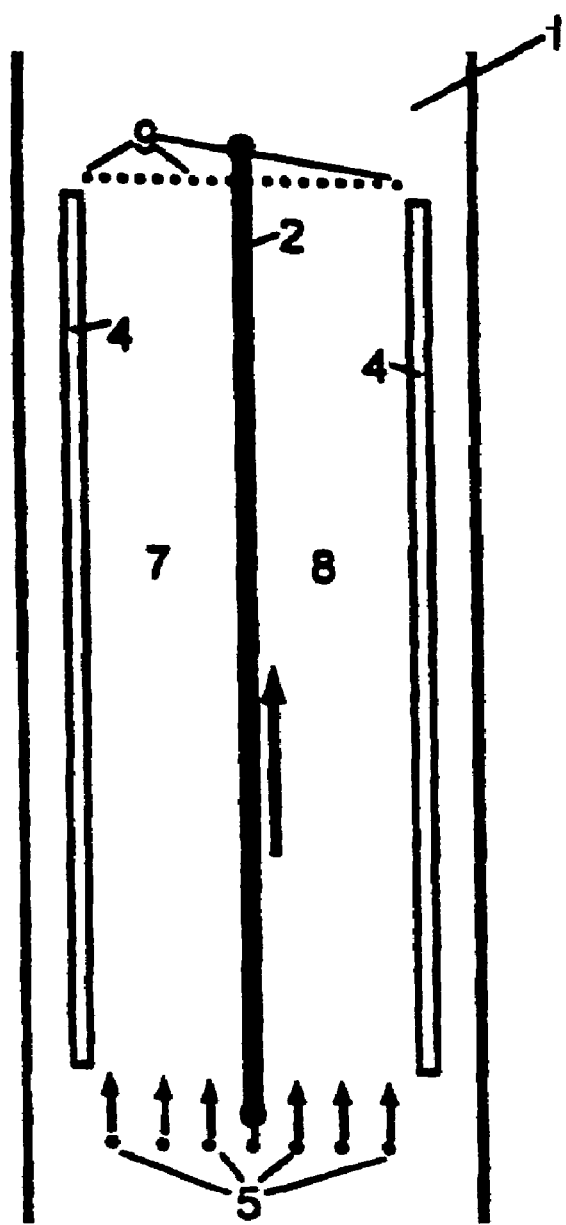
FIG. 1 is a plan view of a first embodiment of the electrophoresis device according to the invention.

The embodiment of the electrophoresis device according to the invention illustrated in FIG. 1 exhibits a horizontally aligned FFE separation chamber with a small gap width of, e.g., 0.3 to 1 mm, which is formed between a synthetic resin block 1 and a metal block 3 having an insulating cover. On the inlet side, the separation chamber is provided with at least one sample inlet and several media inlets 5. On the outlet side, the separation chamber is provided with several outlets 9 for the sample species treated by electrophoresis.

In the separation chamber, a hollow fiber 2 passes from the inlet to the outlet side and separates the separation chamber into two separation chamber parts 7 and 8. Electrodes 4 are arranged parallel to the hollow fiber 2 on both sides of the separation chamber from the inlet to the outlet side. By appropriately poling the direct voltage applied to the electrodes, separation chamber part 7 becomes the separation space for anionic species and the separation chamber part 8 the separation space for cationic species. The electrode voltage is preferably selected in such a way that short migration paths of the species are sufficient for separation.

The hollow fiber 2 is provided with an inlet and an outlet and exhibits in its interior a continuous hollow space leading from the inlet to the outlet. As illustrated in FIG. 1, the hollow fiber 2 extends in the longitudinal direction beyond the outlets 9 for the separated species.

Before being introduced into the separation chamber, the hollow fiber 2 used has an outside diameter substantially larger than the width of the separation chamber spacer, the values of the wall thickness of the hollow fiber 2 being distinctly smaller than half of the width of the separation chamber gap. On introduction of the hollow fiber 2 into the separation chamber, the hollow fiber 2 is flattened in terms of its inner cross-section from a circular shape to an oval shape which, nevertheless, allows the unhindered passage of the sample substances to be separated.

The hollow fiber 2 is arranged parallel to the electrodes 4 within the electrophoretic separation chamber such that once the electrophoresis device illustrated in FIG. 1 is supplied with an aqueous solution with salts dissolved therein and a direct voltage is applied to the electrodes 4, the ionic species in the liquid externally of and within the hollow fiber 2 are moved in the direction of the electrodes. The anionic and cationic species of the salt used migrate in the aqueous solution from the liquid phase through the hollow fiber 2 in the direction of the electrodes 4. Dissolved ionic polymers which, during the electrophoretic migration, reach the interface between the hollow fiber 2 and the aqueous solution, are retained on this interface if the pore size of the hollow fiber 2, compared with the size or the molecular weight of the ionic polymers, is sufficiently small. This retention of the polymeric species occurs equally in the aqueous phase outside the hollow fiber 2 and in the inner hollow space of the hollow fiber 2. The material and the pore size of the hollow fiber 2 differ according to the application concerned, i.e., the samples to be treated, and are chosen correspondingly. The position, i.e., the correct placing of the hollow fiber 2 in the separation chamber, is also chosen as a function of the desired separation of the materials. As an example, a retention of an analyte at the phase boundary of the hollow fiber 2 is possible only if, following the addition of the sample, the migration takes place in the direction towards the hollow fibre.

The electrophoresis device illustrated in FIG. 1 can be used for different applications. In particular, it may be used for electrofiltration under FFE conditions without using it as a separation process; for two-stage separation optimized by making use of the possibilities of both separation processes; for electrofiltration as a measure for sample introduction in order to by-pass complex sample conditioning or to at least simplify it; or for a highly selective electrophoretic separation operation in electrofiltration, i.e., as immunoextraction.

Figure 2:
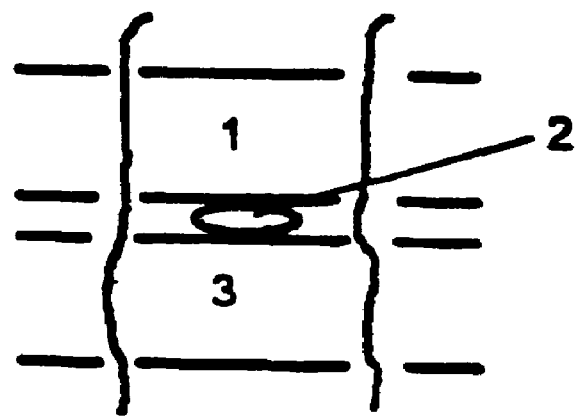
FIG. 2 is a sectional view of the embodiment illustrated in FIG. 1.

FIG. 2 shows a sectional view of the practical example illustrated in FIG. 1.

For electrofiltration, the sample, which is to be fractionated by electrofiltration, can be introduced either via the inner hollow space of the hollow fiber 2 or into the interspace between an electrode 4 and the hollow fiber 2. This is illustrated respectively in FIGS. 3 and 4. In the case of the addition of the sample into the interspace between an electrode 4 and the hollow fiber 2, however, it is necessary to ensure that this addition is effected on the correct side since a retention at the phase boundary between the aqueous phase and the hollow fiber 2 can be expected only if the migration of the polymeric substance takes place in the direction towards the hollow fiber 2.

Figure 3:
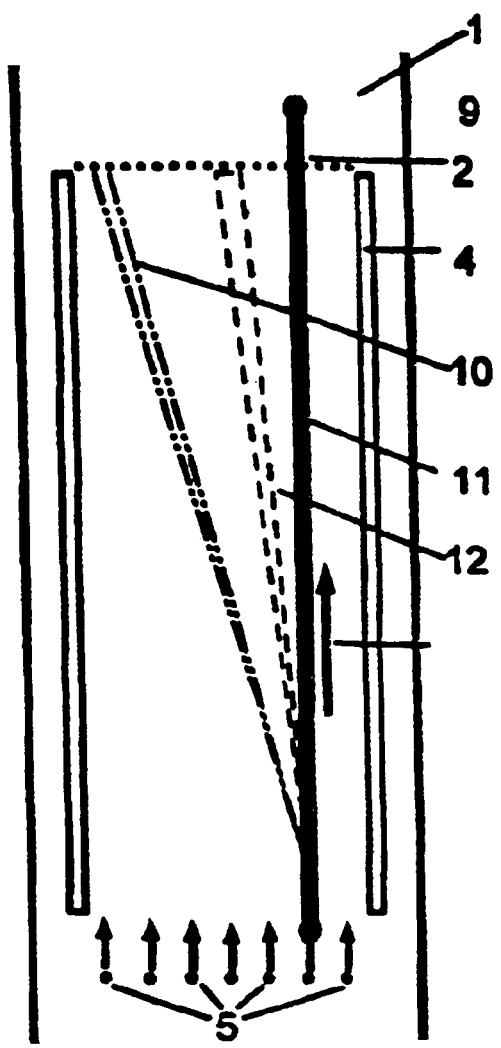
FIG. 3 is a plan view of the embodiment illustrated in FIG. 1 with the introduction of the sample substance in the hollow fiber.

In FIG. 3, in which the addition of the sample into the inner hollow space of the hollow fiber 2 is illustrated, the paths of three analytes are marked as 10, 11, and 12. This means, in particular, that the analyte 11 remains in the hollow fiber 2.

Figure 4:
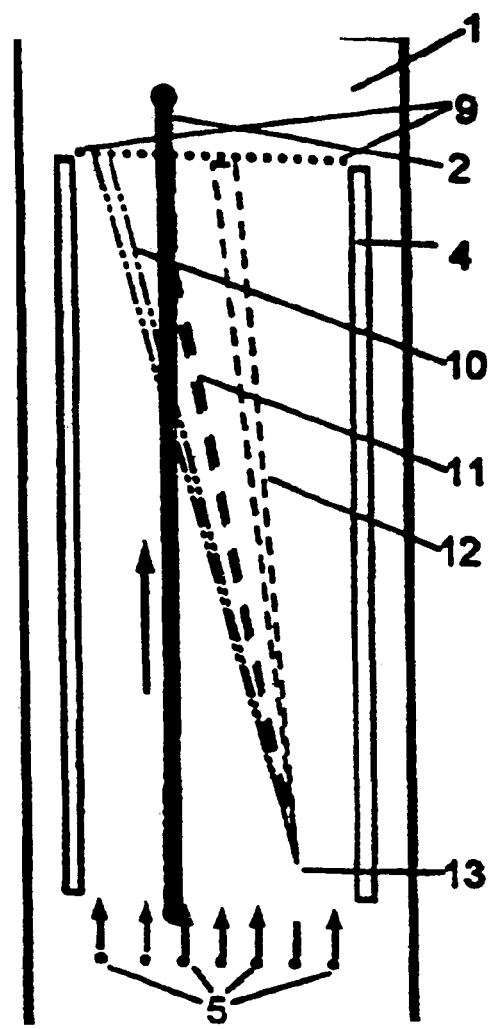
FIG. 4 is a plan view of the embodiment illustrated in FIG. 1 with the introduction of the sample substance into the separation chamber.

In FIG. 4, the paths of the analytes starting out from a sample metering site 13 in the interspace between the hollow fiber 2 and an electrode 4 are also marked as 10, 11 and 12. In the case of this type of application, the analyte 11 is consequently retained on the outer surface, i.e., the interface between the liquid phase and the solid phase.

If the medium within the hollow fiber 2 exhibits different salts and different concentrations of the salts, compared with the medium outside the hollow fiber 2, the original salts within the hollow fiber 2 are substituted by the salts outside the hollow fiber and/or their concentrations are levelled; this is also called sample conditioning.

If the sample conditioned in this way is to be separated in a subsequent independent process, it is eluated from the inner hollow space of the hollow fiber 2, for which purpose the pore size of the hollow fiber 2 is selected to be sufficiently small in order to retain the ionic analytes of interest in the interior of the hollow fiber 2.

If simultaneous sample conditioning and electrophoretic separation by FEE are desirable, a hollow fiber 2 with a pore size must be used which allows the analytes to be separated to be conveyed from the inner hollow space of the hollow fiber 2 into the separation chamber.

An extraction of ionic species between two aqueous solutions is also possible via the sharp interface formed within the separation chamber; this, however, is feasible only if the rheological properties of the media forming this interface for the substance transfer are similar and the adjacent media can be transported through the separation chamber at a similar linear speed. In many cases, however, these boundary conditions are not fulfilled. If a hollow fiber 2 is used for the addition of a medium, the media within and outside of the hollow fiber 2 can be conveyed at different linear speeds and it is even possible to use media with extremely different physical and chemical properties, such as density, viscosity, surface tension, electrical conductivity etc.

The direction of substance transfer and/or migration of the ionic species to be extracted can, in this connection, be selected almost at random; possibilities in this respect are illustrated in FIGS. 3 and 4 and have been described above. This means that the transfer of substance can take place in the direction of the interspace between the hollow fiber 2 and an electrode 4 and along the hollow fiber 2.

Figure 5:
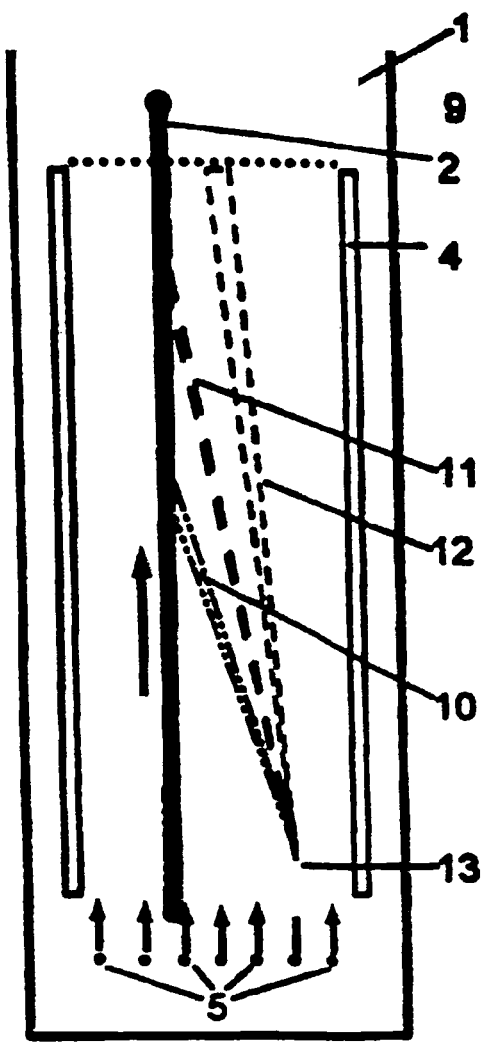
FIG. 5 is a plan view of the embodiment illustrated in FIG. 1 during the so-called immunoextraction.

A further application of the electrophoresis device illustrated in FIG. 1 is the so-called immunoextraction illustrated in FIG. 5. In this application, a component of an immunocomplex to be formed is dissolved in the medium within the hollow fiber 2 in any desired concentration. The molecular weight of this component and/or the separation boundary of the hollow fiber 2 are chosen in such a way that this component remains in the inner hollow space of the hollow fiber 2 even under electrophoresis conditions. As illustrated in detail in FIG. 5, analyte 10 is thus retained in the hollow fiber 2 as immunocomplex, analyte 11 is retained on the outside wall of the hollow fiber 2 and analyte 12 takes the path illustrated in the interspace between the hollow fiber 2 and an electrode 4.

In the case of the combined application of electrofiltration and FFE, conditioning of the sample, which is otherwise frequently necessary before FFE separation, can be omitted. A dilution of the sample is avoidable and can negatively affect or diminish a successful separation and/or the desired sample throughput. The introduction of a sample, which is unsuitable for FFE, a priori, into the separation chamber via the hollow fiber 2 in the way illustrated in FIG. 3, enlarges the field of application of FFE, simplifies the preparation of the sample and handling of the device during routine use and increases the chances of automating the entire separation process.

All FFE separation techniques, i.e., FF zone electrophoresis, FF isotachophoresis, FF isoelectric focusing and FF field jump electrophoresis, can be combined with the process of electrofiltration. In this respect, the combination with focusing FF separation techniques is particularly advantageous.

Figure 6:
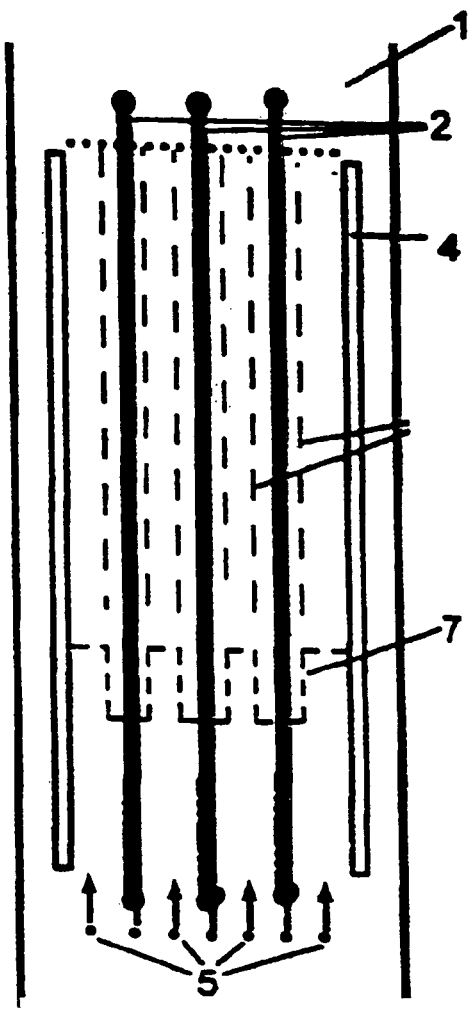
FIG. 6 is a plan view of an embodiment of the electrophoresis device according to the invention, which corresponds to the embodiment illustrated in FIG. 1, but which operates according to a simultaneous multiple process.

The combination of the separation technique of FF field jump electrophoresis with electrofiltration, in particular, provides the possibility of effecting the separation in a parallel simultaneous multiple process with an increased sample throughput. This combination in the form of a triple parallel simultaneous multiple process is illustrated in FIG. 6 in which the interface of the media 6 (concentration of the ionic analytes) and the conductivity profile 7 are illustrated.

The combination of electrofiltration with the focusing FFE separation technique of FF isoelectric focusing and FF isotachophoresis provides an even better separation performance than the above-mentioned combination, although the execution of a simultaneous parallel process is not possible within the separation chamber.

Figure 7:
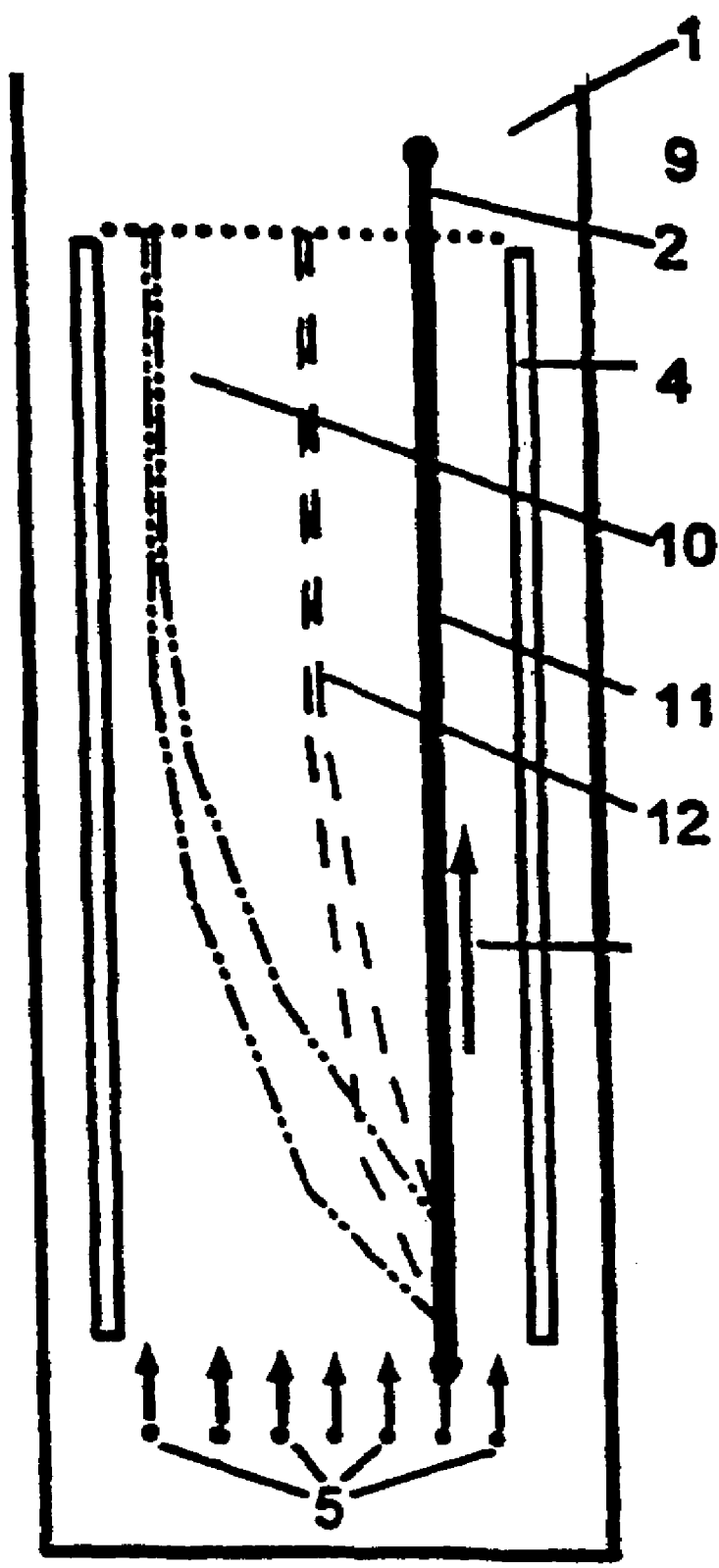
FIG. 7 shows a plan view of the embodiment illustrated in FIG. 1 in combination with FF isoelectric focusing.

FIG. 7 shows the combination of electrofiltration with the separation technique of FF isoelectric focusing, whereby it is possible to transfer the substances to be separated alternatively from the hollow fiber 2 into the interspace between the hollow fiber 2 and the electrodes 4 or from this interspace into the hollow fiber 2, as has already been illustrated in FIGS. 3 and 4. The paths of the analytes are marked by 10 and 12, analyte 11 remains in the hollow fiber 2.

Figure 8A:
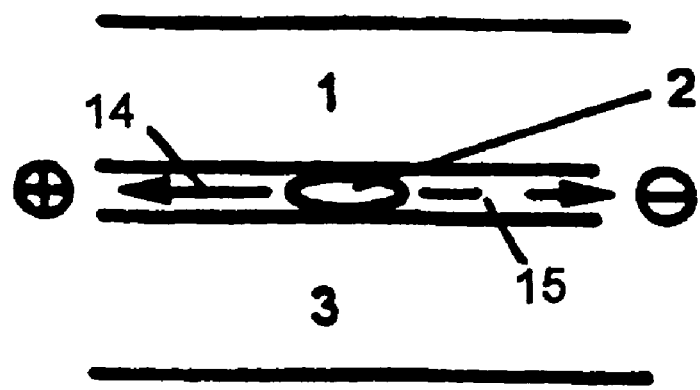
FIGS. 8A to 8C show sectional views of further embodiments of the device according to the invention to illustrate the shape of the separation element.
Figure 8B:
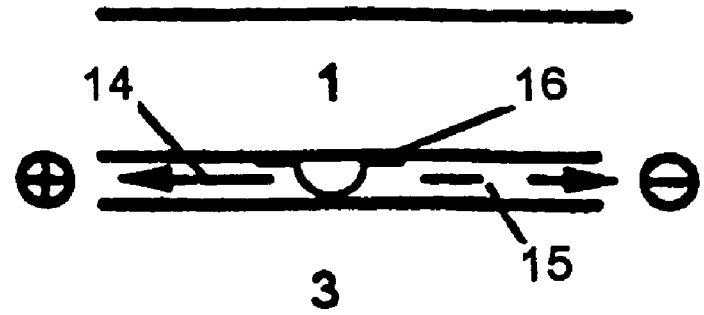
Figure 8C:
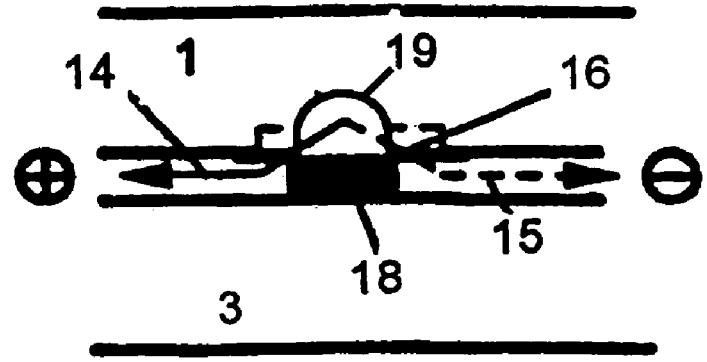

In FIGS. 8B and 8C, the alternative designs regarding the arrangement of a hollow fiber 2 are illustrated; they are shown once more in FIG. 8A for comparison. Here, the migration of the anions and cations is marked as 14 and 15.

FIG. 8B shows a practical example in which a flat membrane 16 is bonded to the inside surface of blocks 1 or 3, preferably to the inside surface of the synthetic resin block 1 such that a hollow space is formed between the inside surface of the synthetic resin block 1 and the flat membrane 16, the height of this hollow space being greater than the width of the separation chamber gap. Consequently, the flat membrane 16 divides the separation chamber in the same way as can be achieved by the hollow fiber 2 in the practical example illustrated in FIG. 8A.

The introduction and discharge of the medium into or out of the hollow space in the flat membrane 16 takes place, in this case, via holes in the synthetic resin block 1.

In the practical example illustrated in FIG. 8C, a groove-type depression 19 is formed in the inner surface of preferably the synthetic resin block 1, instead of a pre-manufactured hollow fiber 2, and the holes for the introduction and discharge are covered with a flat membrane 16. In this way, a channel is formed which is filled with the sample to be separated. By shut-off 18 of the flow transport in the separation chamber above the flat membrane, the electrophoretic conveying of substance is deflected via the flat membrane 16 and the depression 19 in the synthetic resin block 1. The ionic species are then transferred from the depression 19 via the flat membrane into the separation chamber. If necessary, the liquid of the depression 19 can be thermostabilised by means of external cooling.

As previously discussed, the permeability of the filter membrane decreases during pressure filtration as the duration of filtration increases and the content of polymers in the solution to be filtered increases at a more rapid pace. This decrease in the permeability of the filter membrane may be referred to as fouling in the membrane.

In the case of electrofiltration, on the other hand, the significance of fouling is considerably less pronounced since not the entire sample volume but only the ionic species in the sample are conveyed in the direction of the separation membrane; however, the influence of fouling is no longer negligible with high contents of ionic polymeric species which need to be retained on the separation membrane during a prolonged duration of filtration.

In contrast to pressure filtration, in the case of which filtration with a cross-flow is known as a suitable countermeasure to reduce fouling, a cross-flow is achieved in the case of electrofiltration by the flow rate of the sample in the hollow fibre. But the flow rate is optimized not with regard to reducing fouling but to optimize the mass transfer via the membrane. In other words, this means that the cross-flow existing during electrofiltration is insufficient to effectively reduce or eliminate fouling.

A measure for reducing fouling further involves the selection of a pH of the solution to be filtered at which the charge on the polymers is reduced. In the case of biopolymers with amphoteric properties, a pH of the solution is selected which corresponds to the pH of the biopolymer or its main components. This means that the polymer remains unaffected by the electrical field strength.

The following modified electrofiltration process is considerably more effective in eliminating fouling: In the case of the standard process of electrofiltration, a certain direct voltage or a certain electrical field strength is applied throughout the entire period of electrofiltration. With an increasing duration of electrofiltration, the inside surface of the hollow fiber and the space in the pores of the separation membrane are increasingly taken up by ionic polymers, possibly leading to the complete coverage of the inside surface of the separation membrane. As shown in FIG. 9A, this results in a substantial reduction in the mass transfer via the membrane.

By periodically connecting and disconnecting the effective direct voltage, fouling can be reduced substantially since a major portion of the polymer attached to the membrane during the electrofiltration period is conveyed further in the hollow fiber during the period of disconnected direct voltage and can be eluated from the hollow fiber after many periodic alternating connection and disconnection operations. This is illustrated in FIG. 9B.

As a result of the unfavourable flow profile of the laminar flow in the inner space of the hollow fibre, polymers which are in the direct vicinity of the surface of the membrane are eluated only very slowly and the polymers in the pores remain unaffected by the measures of periodic connecting and disconnecting of the direct voltage. If, however, a process is used in the case of which, after a certain period of active electrofiltration, the polarity of the direct voltage is changed, though for a much shorter period, the polymers that have migrated into the pores are drawn in the direction of the opposite inside wall of the hollow fibre. If the duration of the reverse direct voltage is chosen such that a major proportion of the polymers is moved, during this period of the separation process, from the peripheral area and/or the pores into the centre of the hollow fibre, the polymers get into the area of maximum flow rate. As a result, the polymers are highly effectively conveyed further within the hollow fiber and eluated following a few electrofiltration cycles and the effect of the changed polarity. This is illustrated in FIG. 9C.

Active flushing of the wall surfaces and the pores by means of electrophoresis can additionally be enhanced by periodically changing the pressure within the hollow fiber such that, during the period of active electrophoretic flushing, the inside pressure in the hollow fiber is also reduced in comparison with the outside space. In this way, flushing is enhanced by simultaneous pressure flushing in the same direction.

What is claimed is:

1. An electrophoresis device comprising:
a separation chamber having an inlet side with at least one sample inlet and an outlet side having outlets for electrophoretically treated sample species;
at least one separation element selectively permeable to certain samples species, having a longitudinally extending continuous inner hollow space, which is arranged in the separation chamber from the inlet side to the outlet side and divides the separation chamber into two chamber parts; and
electrodes which are arranged on opposing sides of the separation chamber parallel to the separation element, wherein the separation element is formed by a groove-shaped depression in an inside surface of the separation chamber and a facing shut-off device of the separation chamber, and wherein the separation element contains holes between the separation chamber and the groove-shaped depression for introduction and discharge.

2. The electrophoresis device according to claim 1, wherein the holes are covered by a flat membrane.

3. The electrophoresis device according to claim 1, wherein the sample inlet leads into the inner hollow space of the separation element.

4. The electrophoresis device according to claim 1, wherein the sample inlet leads into a part of the separation chamber.

5. The electrophoresis device according to claim 1, wherein a plurality of separation elements are provided parallel to each other and capable of carrying out a simultaneous multiple electrophoresis in the separation chamber.

6. An electrophoresis method, comprising the steps of providing an electrophoresis device having
a separation chamber having an inlet side with at least one sample inlet and an outlet side having outlets for electrophoretically treated sample species;
at least one separation element selectively permeable to certain samples species, having a longitudinally extending continuous inner hollow space, which is arranged in the separation chamber from the inlet side to the outlet side and divides the separation chamber into two chamber parts; and
electrodes which are arranged on opposing sides of the separation chamber parallel to the separation element;
applying a direct voltage to the electrodes of said electrophoresis device; and
periodically connecting and disconnecting said direct voltage during active electrophoresis.

7. The electrophoresis method according to claim 6, wherein a temperature gradient in the separation chamber is maintained as low as possible.

8. An electrophoresis method, comprising the steps of providing an electrophoresis device having
a separation chamber having an inlet side with at least one sample inlet and an outlet side having outlets for the electrophoretically treated sample species;
at least one separation element selectively permeable to certain samples species, having a longitudinally extending continuous inner hollow space, which is arranged in the separation chamber from the inlet side to the outlet side and divides the separation chamber into two chamber parts; and
electrodes which are arranged on opposing sides of the separation chamber parallel to the separation element; and
applying a direct voltage, the polarity of which is periodically reversed, to the electrodes of said electrophoresis device, wherein an application period with a polarity of the direct voltage opposite to a polarity of the direct voltage during active electrophoresis is shorter than the period of the polarity of the direct voltage during active electrophoresis.

9. The electrophoresis method according to claim 8, wherein a temperature gradient in the separation chamber is maintained as low as possible.

10. The electrophoresis method according to claim 8, comprising the further step of periodically altering the inside pressure of the separation element, as compared to the surrounding external space.

11. An electrophoresis device comprising:
a separation chamber having an inlet side with at least one sample inlet and an outlet side having outlets for electrophoretically treated sample species;
at least one separation element selectively permeable to certain samples species, having a longitudinally extending continuous inner hollow space, which is arranged in the separation chamber from the inlet side to the outlet side and divides the separation chamber into two chamber parts; and
electrodes which are arranged on opposing sides of the separation chamber parallel to the separation element, wherein the sample inlet introduces a sample into an interspace between the separation element and the electrodes.

12. An electrophoresis device comprising:
a separation chamber having an inlet side with at least one sample inlet and an outlet side having outlets for the collection of electrophoretically treated sample species;
at least one separation element selectively permeable to certain samples species, having a longitudinally extending continuous inner hollow space, which is arranged in the separation chamber from the inlet side to the outlet side and divides the separation chamber into separation spaces; and
electrodes which are arranged on opposing sides of the separation chamber parallel to the separation element, wherein the outlets for the collection of electrophoretically treated sample species are outside the separation element.

13. An electrophoresis device comprising:

a separation chamber having an inlet side with at least one sample inlet and an outlet side having outlets for the collection of electrophoretically treated sample species;

a plurality of separation elements, arranged parallel to each other, each separation element selectively permeable to certain samples species, having a longitudinally extending continuous inner hollow space, which is arranged in the separation chamber from the inlet side to the outlet side and divides the separation chamber into separation spaces; and electrodes which are arranged on opposing sides of the separation chamber parallel to the separation element, wherein the outlets for the collection of electrophoretically treated sample species are located in the separation spaces.

* * * * *